US012653549B2

(12) United States Patent
Hage et al.

(10) Patent No.: US 12,653,549 B2
(45) Date of Patent: Jun. 16, 2026

(54) SYSTEMS AND METHODS FOR MONITORING A SURGICAL TOOL

(71) Applicant: Medtronic Navigation, Inc., Lafayette, CO (US)

(72) Inventors: Richard Todd Hage, Castle Rock, CO (US); Mark Feuer, New York, NY (US)

(73) Assignee: Medtronic Navigation, Inc., Lafayette, CO (US)

( * ) Notice: Subject to any disclaimer, the term of this patent is extended or adjusted under 35 U.S.C. 154(b) by 92 days.

(21) Appl. No.: 18/659,563

(22) Filed: May 9, 2024

(65) Prior Publication Data

US 2024/0382216 A1     Nov. 21, 2024

Related U.S. Application Data

(60) Provisional application No. 63/466,582, filed on May 15, 2023.

(51) Int. Cl.
| | |
|---|---|
| *A61B 17/16* | (2006.01) |
| *A61B 34/30* | (2016.01) |
| *A61B 34/32* | (2016.01) |
| *A61B 17/00* | (2006.01) |
| *A61B 34/20* | (2016.01) |
| *A61B 90/00* | (2016.01) |

(52) U.S. Cl.
CPC ...... *A61B 17/1626* (2013.01); *A61B 17/1628* (2013.01); *A61B 34/32* (2016.02); *A61B 2017/00022* (2013.01); *A61B 2034/2048* (2016.02); *A61B 2034/2055* (2016.02); *A61B 2090/064* (2016.02)

(58) Field of Classification Search
CPC . A61B 17/1626; A61B 17/1628; A61B 34/32; A61B 2034/2048; A61B 2034/2055; A61B 2090/064; A61B 2017/00022
USPC ....................................................... 606/80, 1
See application file for complete search history.

(56) References Cited

U.S. PATENT DOCUMENTS

| | | | |
|---|---|---|---|
| 9,498,231 B2 | 11/2016 | Haider et al. | |
| 2005/0116673 A1* | 6/2005 | Carl ................... | A61B 17/1626 318/432 |
| 2006/0142657 A1* | 6/2006 | Quaid ................... | A61B 90/37 600/424 |
| 2010/0190133 A1* | 7/2010 | Martinez ............ | A61C 17/0208 604/319 |

(Continued)

FOREIGN PATENT DOCUMENTS

| | | |
|---|---|---|
| CN | 115192199 | 10/2022 |
| WO | WO 2013/052187 | 4/2013 |

(Continued)

OTHER PUBLICATIONS

International Search Report and Written Opinion for International (PCT) Patent Application No. PCT/IB2024/054706, dated Sep. 3, 2024, 13 pages.

*Primary Examiner* — Jessica Weiss
(74) *Attorney, Agent, or Firm* — Sheridan Ross PC

(57) ABSTRACT

Systems and methods for monitoring a surgical tool are provided. A surgical tool may be advanced and rotated and sensor data from a sensor may be received. The sensor data may have a first value that is converted to a second value. A notification may be generated when the second value meets or exceeds a predetermined threshold.

20 Claims, 5 Drawing Sheets

(56) References Cited

U.S. PATENT DOCUMENTS

| | | | | |
|---|---|---|---|---|
| 2011/0152612 A1* | 6/2011 | Trusty | ............... | A61B 1/00135 |
| | | | | 600/109 |
| 2011/0257661 A1* | 10/2011 | Choi | ................. | A61B 1/00094 |
| | | | | 606/130 |
| 2014/0135773 A1* | 5/2014 | Stein | ..................... | A61B 34/20 |
| | | | | 606/100 |
| 2015/0088183 A1* | 3/2015 | Vipperman | ........ | A61B 17/1695 |
| | | | | 606/172 |
| 2018/0157238 A1 | 6/2018 | Gogarty et al. | | |
| 2018/0289432 A1 | 10/2018 | Kostrzewski et al. | | |
| 2021/0161542 A1 | 6/2021 | Kafoury | | |
| 2021/0244487 A1* | 8/2021 | Beck | ................. | A61B 17/1626 |
| 2021/0259781 A1* | 8/2021 | Forstein | ................ | A61B 5/742 |
| 2022/0240951 A1 | 8/2022 | Detinis | | |
| 2022/0257320 A1 | 8/2022 | Junio et al. | | |

FOREIGN PATENT DOCUMENTS

| | | |
|---|---|---|
| WO | WO 2016/172370 | 10/2016 |
| WO | WO 2016/199152 | 12/2016 |
| WO | WO 2022/149139 | 7/2022 |

* cited by examiner

100

102

SYSTEMS AND METHODS FOR MONITORING A SURGICAL TOOL

CROSS REFERENCE TO RELATED APPLICATIONS

This application claims the benefit of U.S. Provisional Application No. 63/466,582, filed on May 15, 2023, and entitled "Systems and Methods for Monitoring a Surgical Tool", which application is incorporated herein by reference in its entirety.

BACKGROUND

The present disclosure is generally directed to surgical tools, and relates more particularly to monitoring a surgical tool based on sensor data from at least one sensor.

Surgical robots may assist a surgeon or other medical provider in carrying out a surgical procedure, or may complete one or more surgical procedures autonomously. Providing controllable linked articulating members allows a surgical robot to reach areas of a patient anatomy during various medical procedures.

BRIEF SUMMARY

Example aspects of the present disclosure include:

A system for monitoring a surgical tool according to at least one embodiment of the present disclosure comprises a surgical tool configured to perform a task on an anatomical element; a motor configured to rotate the surgical tool; at least one sensor configured to sense at least one value of the surgical tool and yield sensor data; and a controller having a processor and a memory storing data for processing by the processor, the data, when processed, causes the processor to: advance and rotate the surgical tool, receive the sensor data, the sensor data having a first value of the at least one value, convert the sensor data from the first value to a second value, and generate a notification when the second value meets or exceeds a predetermined threshold.

Any of the aspects herein, wherein the surgical tool comprises a drilling tool and the task comprises drilling the anatomical element.

Any of the aspects herein, further comprising a printed circuit board (PCB) configured to connect the at least one sensor and the controller.

Any of the aspects herein, wherein the at least one sensor comprises an accelerometer, the sensor data comprises accelerometer data, the first value comprises acceleration values, and the second value comprises vibration values.

Any of the aspects herein, wherein the sensor data is converted using a power spectral density conversion.

Any of the aspects herein, further comprising a robotic arm configured to orient the surgical tool and advance the surgical tool.

Any of the aspects herein, wherein the at least one sensor comprises a pressure sensor and the memory stores further data for processing by the processor that, when processed, causes the processor to: cause the motor to stop rotation of the surgical tool when the first value meets or exceeds a predetermined threshold.

Any of the aspects herein, further comprising a housing configured to house the surgical tool.

Any of the aspects herein, wherein the housing forms a tube having an opening through which the surgical tool extends from, wherein debris is suctioned from the opening to a discharge tube.

Any of the aspects herein, wherein the at least one sensor comprises a pressure sensor and the sensor data comprises pressure data, and wherein the surgical tool is advanced when the pressure data is below the predetermined threshold.

A system for monitoring a surgical tool according to at least one embodiment of the present disclosure comprises a surgical tool configured to drill an anatomical element; a motor configured to rotate the surgical tool; at least one accelerometer configured to sense accelerometer data and yield acceleration sensor data; and a controller having a processor and a memory storing data for processing by the processor, the data, when processed, causes the processor to: cause the motor to rotate and advance the surgical tool, receive acceleration sensor data from the at least one accelerometer, the acceleration sensor data having acceleration values, convert the acceleration values to vibration values, and generate a notification when the vibration values meets or exceeds a predetermined threshold.

Any of the aspects herein, wherein the acceleration values are converted using a power spectral density conversion.

Any of the aspects herein, further comprising a robotic arm configured to autonomously operate and orient the surgical tool.

A system for monitoring a surgical tool according to at least one embodiment of the present disclosure comprises a surgical tool configured to drill an anatomical element; a motor configured to rotate the surgical tool; at least one sensor configured to sense at least one value of the surgical tool and yield sensor data; and a controller having a processor and a memory storing data for processing by the processor, the data, when processed, causes the processor to: cause the motor to rotate and advance the surgical tool, receive the sensor data, the sensor data having the at least one value, and generate a notification when the at least one value meets or exceeds a predetermined threshold.

Any of the aspects herein, further comprising a clutch configured to prevent the motor from rotating the surgical tool when the at least one value meets or exceeds the predetermined threshold.

Any of the aspects herein, wherein the at least one sensor comprises a pressure sensor and the memory stores further data for processing by the processor that, when processed, causes the processor to: cause the motor to stop rotation of the surgical tool when the at least one value meets or exceeds a predetermined threshold.

Any of the aspects herein, further comprising a housing configured to house the surgical tool.

Any of the aspects herein, further comprising a camera positioned on the housing.

Any of the aspects herein, wherein the housing forms a tube having an opening through which the surgical tool extends from, wherein debris is suctioned from the opening to a discharge tube.

Any of the aspects herein, wherein the at least one sensor comprises a pressure sensor and the sensor data comprises pressure data, and wherein the surgical tool is advanced when the pressure data is below the predetermined threshold.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present disclosure will become apparent to those skilled in the art upon consideration of the embodiment descriptions provided hereinbelow.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
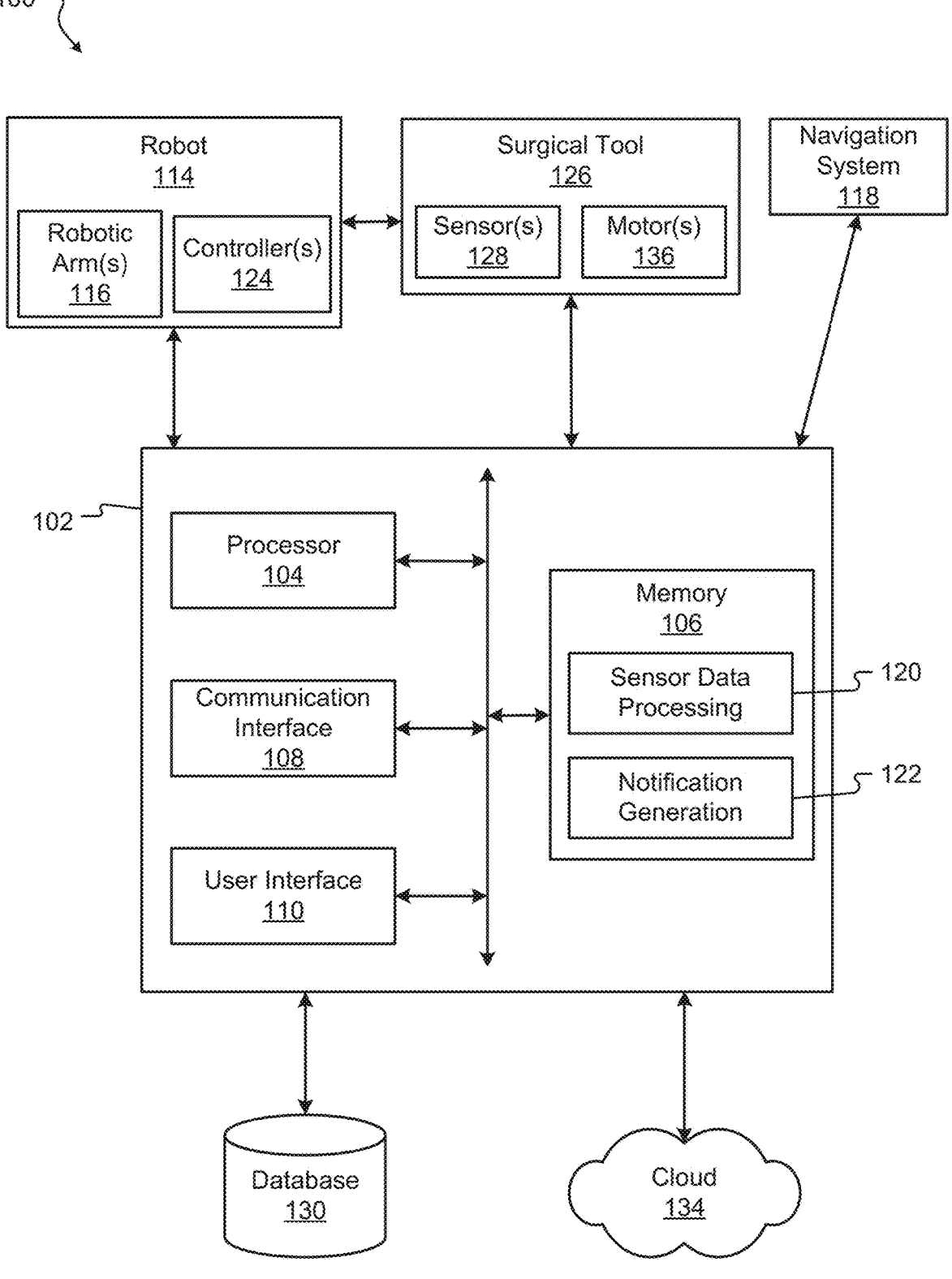
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia Geforce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

Surgical tools such as, for example, drilling tools, used during surgical procedures perform optimally when the drilling tool (or any other surgical tool) is drilling at an expected speed and torque. However, components such as, for example, internal bearings may wear and affect the expected speed and torque. When the bearings being to fail, a vibration signature of the drilling tool often changes. Thus, a change in this vibration signature using a sensor such as, for example, an accelerometer can be used to monitor the vibration signature.

Systems and methods according to at least one embodiment of the present disclosure provides for at least one sensor positioned on or integrated with the surgical tool. The sensor can be an accelerometer and the acceleration data can be sent to a sensing printed circuit board (PCB) which converts the acceleration data to input signals for a controller. The sensing PCB can be mounting on a robotic arm or within a base or platform cart of a robot. The controller can convert the acceleration values to vibration values using a Power spectral density conversion, though it will be appreciated that the controller can convert any first values to a second value. The vibration values are then compared to nominal vibration values. If the vibration values are off-nominal then the acceleration data are flagged as indicating potential bearing failure. A display signal may also be shown indicating the potential failure, allowing a user such as, for example, a surgeon to decide whether the surgical procedure should proceed.

The systems and methods according to at least one embodiment of the present disclosure also provides for using surgical tool(s) autonomously using, for example, a robot or robotic arm. The sensor data can be used as feedback to the robotic arm (and more specifically, a controller of the robot) to monitor the surgical tool and control the surgical tool. It will be appreciated that the surgical tool and the described systems and methods can be used in any surgical procedure such as cranial surgery, spinal surgery, etc.

Embodiments of the present disclosure provide technical solutions to one or more of the problems of (1) monitoring a surgical tool using one or more sensors, (2) determining whether a surgical tool may fail, and (3) increasing patient safety.

Turning first to FIG. 1, a block diagram of a system 100 according to at least one embodiment of the present disclosure is shown. The system 100 may be used to optimize use of a surgical tool and/or carry out one or more other aspects of one or more of the methods disclosed herein. The system 100 comprises a computing device 102, a robot 114, one or more controller(s) 124, one or more surgical tool(s) 126, a navigation system 118, a database 130, and/or a cloud or other network 134. Systems according to other embodiments of the present disclosure may comprise more or fewer components than the system 100. For example, the system 100 may not include the robot 114, the controller 124, the navigation system 118, one or more components of the computing device 102, the database 130, and/or the cloud 134.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the controller 124, the surgical tool 126 (more specifically, at least one sensor 128 of the surgical tool 126), the robot 114, the navigation system 118, the database 130, and/or the cloud 134.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the method 400 described herein, or of any other methods. The memory 106 may store, for example, instructions and/or machine learning models that support one or more functions of the robot 114. For instance, the memory 106 may store content (e.g., instructions and/or machine learning models) that, when executed by the processor 104 or the controller 124, enable sensor data processing 120 and/or notification generation 122.

The sensor data processing 120 enables the processor 104 (or a processor of a printed circuit board (PCB) 202 (shown in FIGS. 2A-2B) to process sensor data (received from for example, the sensor 128) into input signals. The input signals can then be converted by, for example, the controller 124 using the sensor data processing 120 to convert the input signals from a first value to a second value. The first value may comprise, for example, acceleration value(s) and the second value may comprise vibration value(s). In other embodiments the first value and/or the second value may comprise any value such as, for example, pressure value(s), acceleration value(s), force value(s), vibration value(s), etc. The processor 104 may use a power spectral density conversion to convert the first value to the second value. In other embodiments, the processor 104 may use any conversion to convert the first value to the second value.

The notification generation 124 enables the processor 104 to generate a notification when a value such as the first value or the second value meets or exceeds a predetermined threshold. It will be appreciated that in some embodiments, the notification may be generated when the first value or the second value is below the predetermined threshold. In still other embodiments, the notification may be generated when a difference between the first value and an expected first value or the second value and an expected second value meets or exceeds the predetermined threshold. The notification may be an audible and/or a visual notification (which may be displayed on, for example, the user interface 110).

In some examples, the second value may include vibration values that are compared to nominal vibration values. If a difference between the vibration values and the nominal vibration values meet or exceed the predetermined threshold, indicating that the vibration values are off-nominal, then the processor 104 may generate a notification to indicate that the difference between the vibration values and the nominal vibration values have met or exceeded the predetermined threshold. When the vibration values are off-nominal, this may indicate that one or more bearings 204 (shown in FIG. 2A) of the surgical tool 126 may be failing or potentially failing.

In other examples, the first value may include pressure values and the surgical tool 126 may be advanced when the pressure values are greater than the predetermined threshold. In such examples, the notification may be generated when the pressure values are less than the predetermined threshold. When the pressure values are less than the predetermined threshold, this may indicate that, for example, the surgical tool 126 has completed a pass through of hard tissue.

Such content, if provided as in instruction, may, in some embodiments, be organized into one or more applications, modules, packages, layers, or engines. Alternatively or additionally, the memory 106 may store other types of content or data (e.g., machine learning models, artificial neural networks, deep neural networks, etc.) that can be processed by the processor 104 to carry out the various method and features described herein. Thus, although various contents of memory 106 may be described as instructions, it should be appreciated that functionality described herein can be achieved through use of instructions, algorithms, and/or machine learning models. The data, algorithms, and/or instructions may cause the processor 104 to manipulate data stored in the memory 106 and/or received from or via the controller 124, the sensor 128, the robot 114, the database 130, and/or the cloud 134.

The computing device 102 may also comprise a communication interface 108. The communication interface 108 may be used for receiving sensor data or other information from an external source (such as the controller 124, the sensor 128, the robot 114, the navigation system 118, the database 130, the cloud 134, and/or any other system or component not part of the system 100), and/or for transmitting instructions, images, or other information to an external system or device (e.g., another computing device 102, the controller 124, the sensor 128, the robot 114, the navigation system 118, the database 130, the cloud 134, and/or any other system or component not part of the system 100). The communication interface 108 may comprise one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104, the controller 124, or another component of the system 100) or received by the system 100 from a source external to the system 100. The user interface 110 may also be used to display, for example, a notification. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The robot 114 may be any surgical robot or surgical robotic system. The robot 114 may be or comprise, for example, the Mazor X™ Stealth Edition robotic guidance system. The robot 114 may be configured to position the surgical tool 126 at one or more precise position(s) and orientation(s), and/or to return the surgical tool 126 to the same position(s) and orientation(s) at a later point in time. The robot 114 may additionally or alternatively be configured to manipulate the surgical tool 126 (whether based on guidance from the navigation system 118 or not) to accomplish or to assist with a surgical task. In some embodiments, the robot 114 may be configured to hold and/or manipulate an anatomical element during or in connection with a surgical procedure. The robot 114 may comprise one or more robotic arms 116. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the surgical tool 126. In embodiments where the surgical tool 126 comprises two or more physically separate components (e.g., a transmitter and receiver), one robotic arm 116 may hold one such component, and another robotic arm 116 may hold another such component. Each robotic arm 116 may be positionable independently of the other robotic arm. The robotic arms 116 may be controlled in a single, shared coordinate space, or in separate coordinate spaces.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, the surgical tool 126 or other object held by the robot 114 (or, more specifically, by the robotic arm 116) may be precisely positionable in one or more needed and specific positions and orientations.

The robotic arm(s) 116 may comprise one or more sensors that enable the processor 104 (or a processor of the robot 114 or the controller 124) to determine a precise pose in space of the robotic arm (as well as any object or element held by or secured to the robotic arm).

In some embodiments, reference markers (e.g., navigation markers) may be placed on the robot 114 (including, e.g., on the robotic arm 116), the surgical tool 126, or any other object in the surgical space. The reference markers may be tracked by the navigation system 118, and the results of the tracking may be used by the robot 114 and/or by an operator of the system 100 or any component thereof. In some embodiments, the navigation system 118 can be used to track other components of the system (e.g., surgical tool 126) and the system can operate without the use of the robot 114 (e.g., with the surgeon manually manipulating the surgical tool 126 and/or one or more surgical tools, based on information and/or instructions generated by the navigation system 118, for example).

In the illustrated embodiment, the robot 114 includes the controller 124, though in some embodiments the robot 114 may not include the controller 124. In other embodiments, the controller 124 may be a component separate from the robot 114 and in still other embodiments, the controller 124 may be integrated with the computing device 102. The controller 124 may be an electronic, a mechanical, or an electro-mechanical controller. The controller 124 may comprise or may be any processor described herein. The controller 124 may comprise a memory storing instructions for executing any of the functions or methods described herein as being carried out by the controller 124. In some embodiments, the controller 124 may be configured to simply convert signals received from the computing device 102 (e.g., via a communication interface 108) into commands for operating the robot 114 and/or operating the surgical tool 126. In other embodiments, the controller 124 may be configured to process and/or convert signals received from the sensor 128. Further, the controller 124 may receive signals from one or more sources (e.g., the sensor 128, the computing device 102, the navigation system 118, and/or the robot 114) and may output signals to one or more sources.

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some embodiments, the navigation system 118 may comprise one or more electromagnetic sensors. In various embodiments, the navigation system 118 may be used to track a position and orientation (e.g., a pose) of the surgical tool 126, the robot 114 and/or robotic arm 116, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102, the controller 124, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system

100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

The surgical tool 126 may comprise any surgical tool such as, for example, a drilling tool, a screw driver, and/or a cutting tool. In embodiments where the surgical tool 126 is a drilling tool, the drilling tool may include a burr, a rotary file, a drill bit, or any other type of rotary drilling or cutting implement. The drilling tool may be used to drill through any anatomical element such as hard tissue or soft tissue. For example, the drilling tool may be used in a cranial procedure to drill through a patient's skull. In other examples, the drilling tool may be used in a spinal procedure to drill through or into a patient's vertebra. Similarly, the screw driver may be used in any surgical procedure and may be used to screw an implant into an anatomical element such as, for example, hard tissue.

The surgical tool 126 may include a motor 136 and at least one sensor 128. In some embodiments, the surgical tool 126 may not include the motor 136. The motor 136 is configured to rotate the surgical tool 126 and may receive instructions from, for example, the controller 124, the computing device 102, and/or the robot 114. The motor 136 may be an electric motor, a pneumatic motor, a hydraulic motor, a gear motor, an AC brushless motor, a DC brushed motor, a DC brushless motor, a servo motor, or any other type of motor.

The sensor 128 may be configured to sense at least one value of the surgical tool 126 and yield sensor data. The sensor 128 may correspond to transducers that are configured to convert physical phenomena into an electrical signal that is capable of being processed by the controller 124 or the processor 104 of the computing device 102. Non-limiting examples of the sensor 128 include gyroscopic sensor, pressure sensor, accelerometers, strain gauges, impact sensor, vibration detectors, etc. The sensor 128 may include one or more or any combination of components that are electrical, mechanical, electro-mechanical, magnetic, electromagnetic, or the like. In some embodiments, the sensor 128 may include a memory for storing sensor data. In still other examples, the sensor 128 may output signals (e.g., sensor data) to one or more sources (e.g., the PCB 202, the controller 124, the computing device 102, the navigation system 118 and/or the robot 114).

The sensor 128 may be positioned adjacent to or integrated with the surgical tool 126. In some embodiments, the sensor 128 may be positioned adjacent to or integrated with the robotic arm 116 or the robot 114. In some embodiments, the sensor 128 is positioned as a standalone component. The sensor 128 may include a plurality of sensor and each sensor may be positioned at the same location or a different location as any other sensor. The sensor 128 may send the sensor data to the controller 124 and/or the computing device 102 continuously or for a time period. Further, in some embodiments, the sensor 128 may send data to the computing device 102 to display on the user interface 110 or otherwise notify the surgeon or operator of a change in the sensor data such as, for example, when the values of the sensor data meets or exceeds a predetermined threshold.

The database 130 may store information that correlates one coordinate system to another (e.g., one or more robotic coordinate systems to a patient coordinate system and/or to a navigation coordinate system). The database 130 may additionally or alternatively store, for example, one or more surgical plans (including, for example, pose information about a target and/or image information about a patient's anatomy at and/or proximate the surgical site, for use by the robot 114, the navigation system 118, and/or a user of the computing device 102 or of the system 100); one or more images useful in connection with a surgery to be completed by or with the assistance of one or more other components of the system 100; sensor data; and/or any other useful information. The database 130 may be configured to provide any such information to the computing device 102 or to any other device of the system 100 or external to the system 100, whether directly or via the cloud 134. In some embodiments, the database 130 may be or comprise part of a hospital image storage system, such as a picture archiving and communication system (PACS), a health information system (HIS), and/or another system for collecting, storing, managing, and/or transmitting electronic medical records including image data.

The cloud 134 may be or represent the Internet or any other wide area network. The computing device 102 may be connected to the cloud 134 via the communication interface 108, using a wired connection, a wireless connection, or both. In some embodiments, the computing device 102 may communicate with the database 130 and/or an external device (e.g., a computing device) via the cloud 134.

The system 100 or similar systems may be used, for example, to carry out one or more aspects of any of the method 400 described herein. The system 100 or similar systems may also be used for other purposes.

Figure 2A:
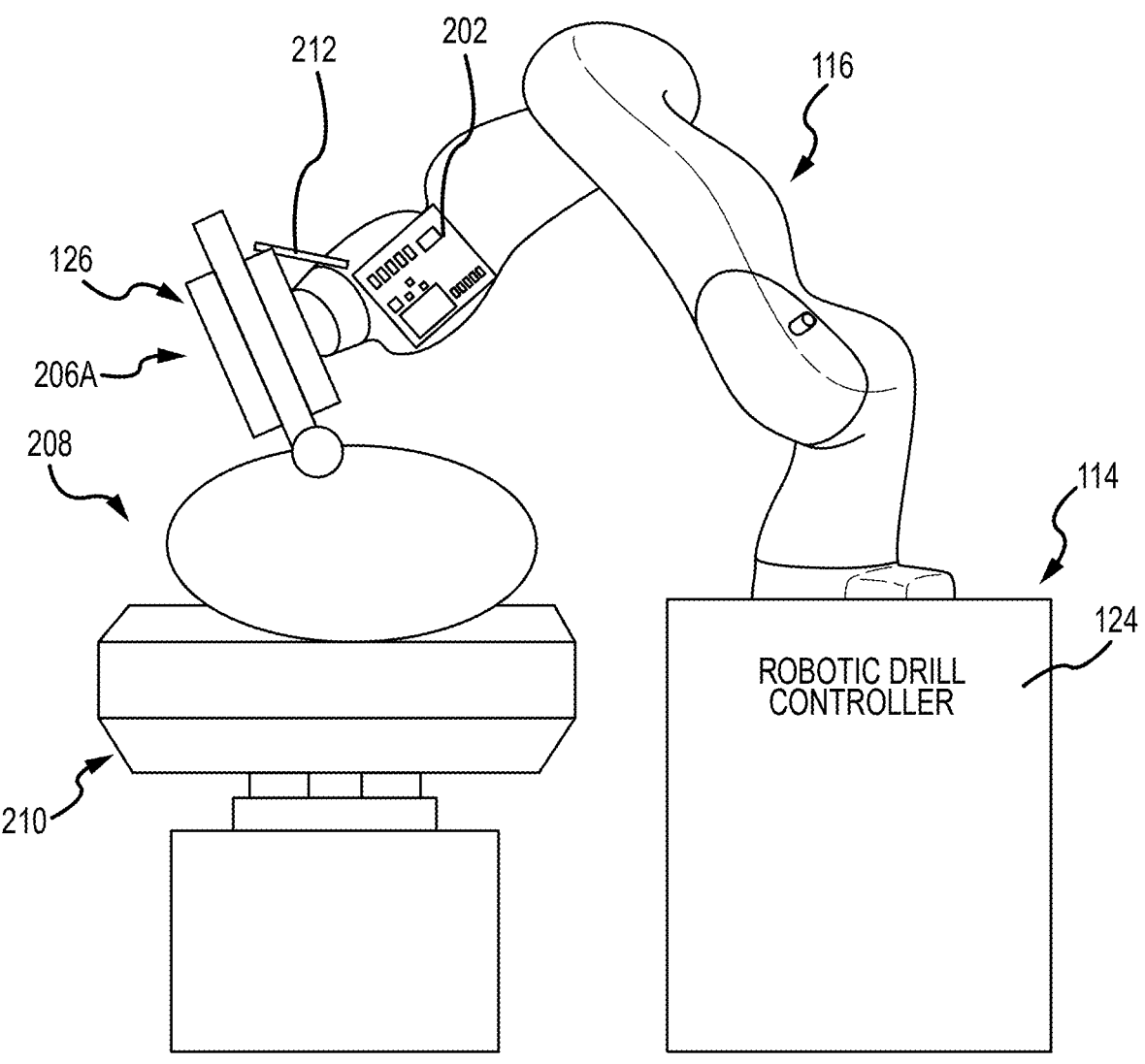
FIG. 2A is a diagram of a robot and a surgical tool according to at least one embodiment of the present disclosure.
Figure 2B:
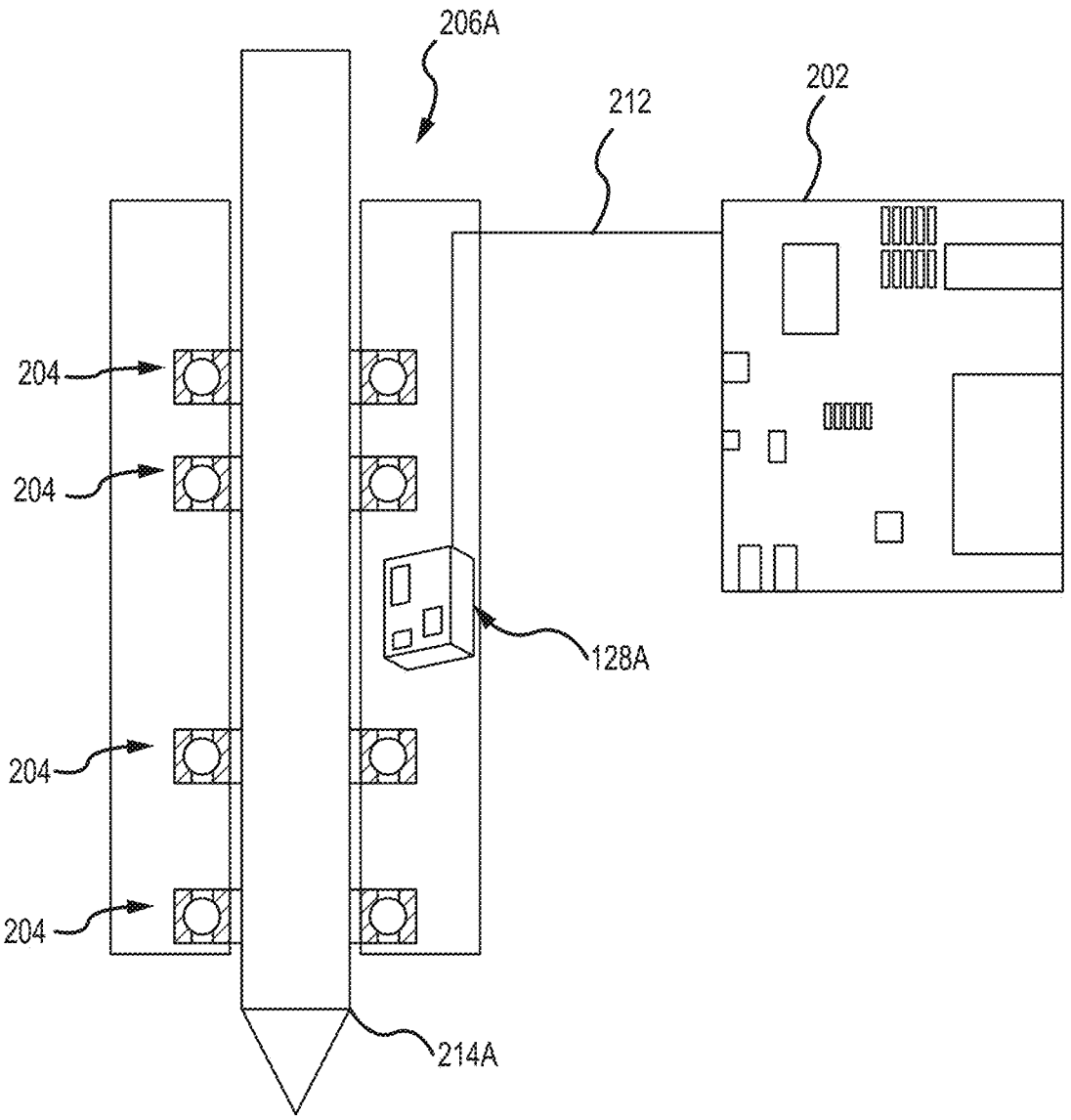
FIG. 2B is a diagram of a surgical tool according to at least one embodiment of the present disclosure.

FIGS. 2A and 2B illustrate at least one embodiment of the surgical tool 126 and the robot 114 and a detailed view of the surgical tool 126, respectively. In the illustrated embodiments, the surgical tool 126 is a drilling tool 206A oriented by the robotic arm 116 of the robot 114. The drilling tool 206A may be autonomously or semi-autonomously (e.g., with input or assistance from a user) oriented and/or operated by the robotic arm 116. In other instances, the drilling tool 206A may be oriented and/or operated by a user such as, for example, a surgeon or other medical provider. The drilling tool 206A may be oriented at a patient 208 positioned on an operating table 210. As illustrated, the drilling tool 206A, and more specifically, the sensor 128 (which may be, for example, an accelerometer) may be connected to the PCB 202 via a wire 212. The PCB 202 is configured to convert the sensor data from the sensor 128 to input signals for the controller 124 (or any processor such as, for example, the processor 104). The PCB may be positioned on the robotic arm 114, as illustrated, or may be positioned on any part of the robot 114 or robotic arm 116.

Turning to FIG. 2B, the drilling tool 206A also includes a drill bit 214A and one or more bearings 204. As previously described, the bearings 204 may begin to fail when a speed and/or a torque of the drilling tool 206A becomes non-optimal. When such failure begins to occur, a vibration value of the drilling tool 206A may change. The vibration value can be determined from converting acceleration values that can be measured by the sensor 128A to the vibration value. Thus, the sensor data from the sensor 128A can be used to determine when the drilling tool 206A is operating sub-optimally, which may indicate bearing failure. In such instances, the drilling tool 206A may no longer operate within parameters and thus, can be removed from service for repair or replacement.

Figure 3:
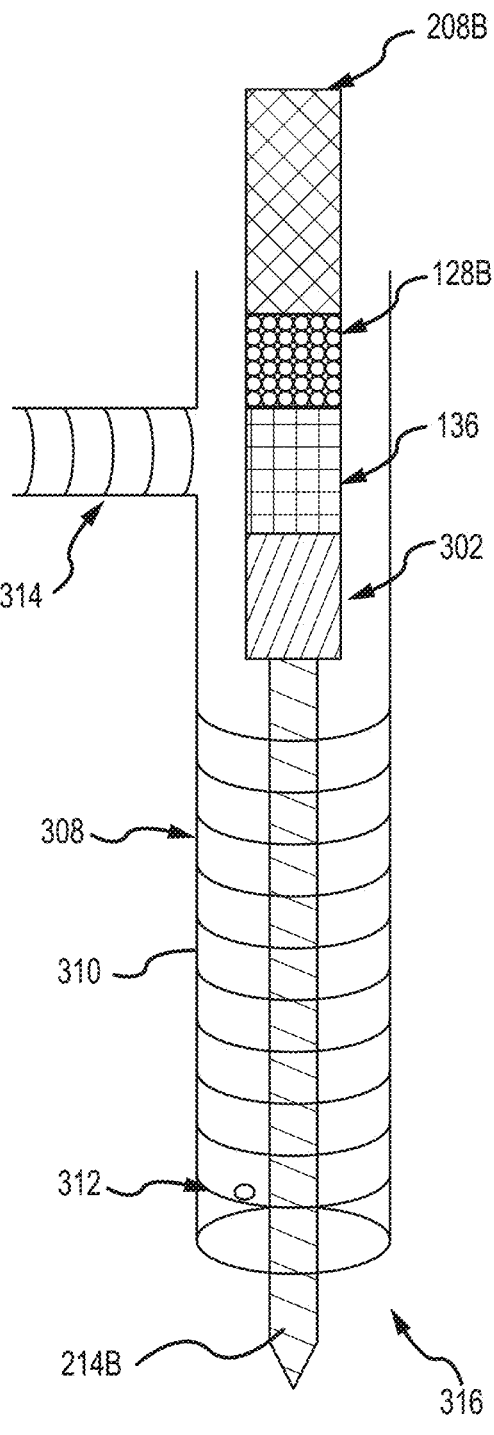
FIG. 3 is a diagram of a surgical tool according to at least one embodiment of the present disclosure.

FIG. 3 illustrates another embodiment of the surgical tool 126 where the surgical tool 126 is another embodiment of the drilling tool 208B. The drilling tool 208B includes a drill bit 214B, the motor 136, the sensor 128B, and a clutch 302. The clutch 302 is configured to prevent the motor 136 from rotating the drill bit 214B when the value of the sensor data meets or exceeds the predetermined threshold. In such embodiments, the sensor data may comprise torque data and when the torque data meets or exceeds a predetermined torque threshold, the clutch 302 may disengage the motor 136 from the drill bit 214B. Such disengagement may prevent the drill bit 214B from applying too much torque to the anatomical element (e.g., hard tissue) and thus, may prevent damage to the anatomical element.

In the illustrated embodiment, the sensor 128B may alternatively or additionally comprise a pressure sensor configured to sense pressure of the drill bit 214B and yield pressure data. The pressure data can be used as feedback to, for example, the controller 124 to determine when to advance the drilling tool 208B and/or when to stop the drilling tool 208B. For example, the drilling tool 208B may be advanced through hard tissue when the pressure data is consistent with a desired pressure and may be stopped when the pressure data decreases and indicates that the drilling tool 208B has passed through the hard tissue.

The drilling tool 208B may include other components such as, for example, a housing 308 in the form of a tube 310 having an opening 316. The drill bit 214B may extend from the opening. The tube 310 may also function as a suction tube and may suction, for example, debris and/or fluids through the suction tube to a discharge tube 314. In such examples, the tube 310 may include an aperture 312 so as to prevent a vacuum in the tube 310 during suctioning. The drilling tool 208B may also include a camera (not illustrated) mounted to the tube 310 to provide a direct view of the drilling site.

It will be appreciated that in some embodiments, the drill bit 214B may comprise a driver for installing screws. In other words, the drill bit 214B may comprise a bit or a driver such that the drilling tool 208B can be used as a screwdriver. In such embodiments, the driver may include a bit or a socket, depending on the type of the screw being installed. For example, a bit may be used to install a screw having a screw head with an internal hex. In another example, a socket may be used to install a screw having a screw head with an external hex. It will be appreciated that the driver may be used to install any type of screw with any type of screw head.

Figure 4:
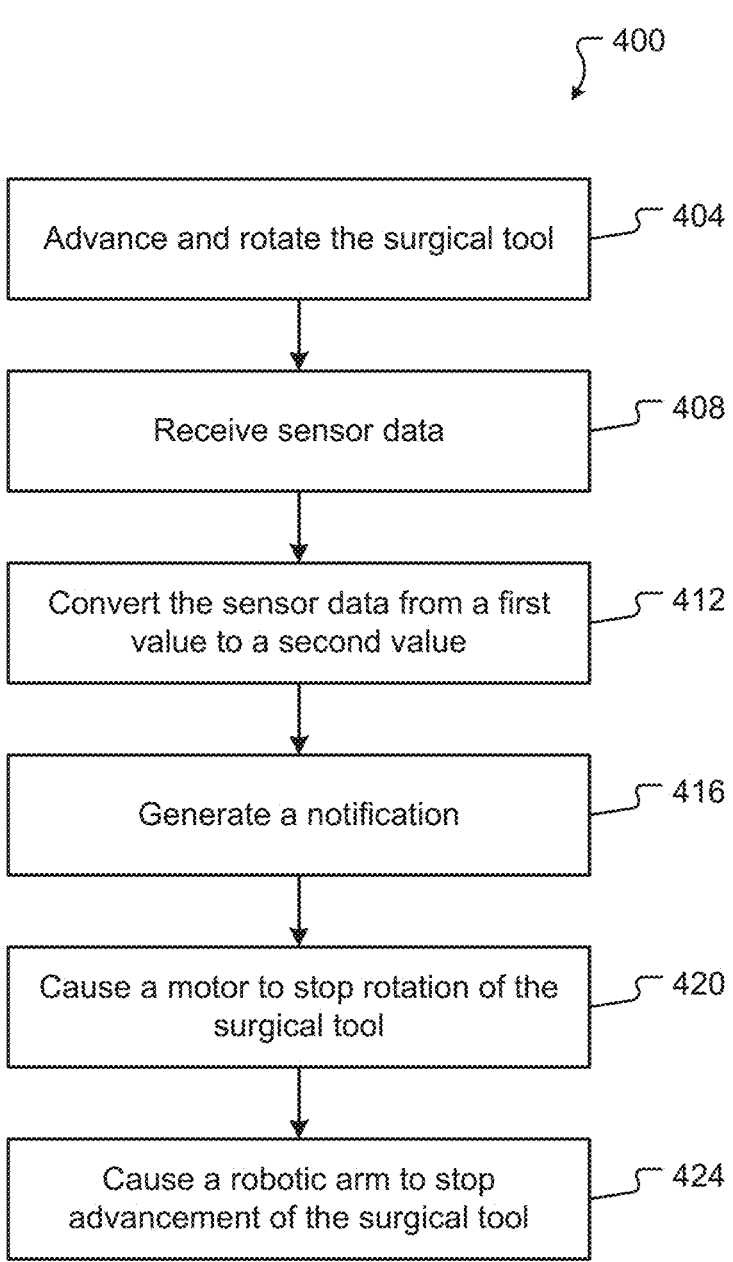
FIG. 4 is a flowchart according to at least one embodiment of the present disclosure.

FIG. 4 depicts a method 400 that may be used, for example, for optimizing a surgical tool such as the surgical tool 126.

The method 400 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 400. The at least one processor may perform the method 400 by executing elements stored in a memory such as the memory 106. The elements stored in memory and executed by the processor may cause the processor to execute one or more steps of a function as shown in method 400. One or more portions of a method 400 may be performed by the processor executing any of the contents of memory, such as sensor data processing 120 and/or notification generation 124.

The method 400 comprises advancing and rotating the surgical tool (step 404). The surgical tool may be the same as or similar to the surgical tool 126. As previously described, the surgical tool may include a drilling tool such as the drilling tool 206A, 206B, though in other embodiments the surgical tool may include, for example, a cutting tool or a screw driver. The surgical tool may be rotated by a motor such as the motor 136, which may be controlled by a controller such as the controller 124. The surgical tool may be advanced by a robot such as the robot 114 or a robotic arm such as the robotic arm 116 the robot 114. More specifically, the surgical tool may be supported, oriented, and/or operated by the robot and/or the robotic arm. In some embodiments, the robot and/or the robotic arm may autonomously or semi-autonomously orient and operate the surgical tool. In other embodiments, a user such as, for example, a surgeon or other medical provider may operate and orient the surgical tool with or without assistance from the robot and/or the robotic arm. For example, the robotic arm and/or the robot may orient the surgical tool at a desired pose and may cause the motor to rotate the surgical tool, and the user may advance the surgical tool.

The method 400 also comprises receiving sensor data (step 408). The sensor data may be received from a sensor such as the sensor 128, 128A, 128B. The sensor data may include, for example, pressure sensor data, acceleration sensor data, force sensor data, and/or torque sensor data. The sensor may be configured to sense at least one value and yield the sensor data. The sensor may correspond to transducers that are configured to convert physical phenomena into an electrical signal that is capable of being processed by the controller or the processor of the computing device. Non-limiting examples of sensor include gyroscopic sensor, pressure sensor, accelerometers, strain gauges, impact sensor, vibration detectors, etc. The sensor may include one or more or any combination of components that are electrical, mechanical, electro-mechanical, magnetic, electromagnetic, or the like. In some embodiments, the sensor may include a memory for storing sensor data. In still other examples, the sensor may output signals (e.g., sensor data) to one or more sources (e.g., the controller, the computing device, the navigation system and/or the robot) and may be stored in memory such as the memory 106 or a memory of the controller or the robot.

The method 400 also comprises converting the sensor data from a first value to a second value (step 412). The sensor data may be processed by a processor such as the processor 104 or a PCB such as the PCB 202 executing a sensor data processing such as the sensor data processing 120 to process the sensor data (received in, for example, the step 408) into input signals. The input signals can then be converted by, for example, the controller using the sensor data processing to convert the input signals from a first value to a second value. The first value may comprise, for example, acceleration value(s) and the second value may comprise vibration value(s). In other embodiments the first value and/or the second value may comprise any value such as, for example, pressure value(s), acceleration value(s), force value(s), vibration value(s), etc. The controller may use a power spectral density conversion to convert the first value to the second value. In other embodiments, the controller may use any conversion to convert the first value to the second value.

In other embodiments the sensor data may be simply processed into input signals and compared to a predetermined threshold. In other words, the sensor data may not be converted from a first value to a second value.

The method 400 also comprises generating a notification (step 416). The notification may be generated by the processor using a notification generation such as the notification generation 124 to generate a notification when a value such as the first value or the second value meets or exceeds a predetermined threshold. It will be appreciated that in some embodiments, the notification may be generated when the first value or the second value is below the predetermined threshold. The notification may be an audible and/or a visual notification (which may be displayed on, for example, the user interface). In still other embodiments, the notification may be generated when a difference between the first value and a desired first value or the second value and a desired second value meets or exceeds the predetermined threshold.

In some examples, the second value may include vibration values that are compared to nominal vibration values. If the vibration values meet or exceed the predetermined threshold, indicating that the vibration values are off-nominal, then the processor 104 may generate a notification to indicate that the vibration values have met or exceeded the predetermined threshold (or that a difference between the vibration values and the nominal vibration values has met or exceeded the predetermined threshold). When the vibration values are off-nominal, this may indicate that one or more bearings such as the one or more bearings 204 of the surgical tool may be failing or potentially failing.

In other examples, the first value may include a pressure value and the surgical tool may be advanced when the pressure value is greater than the predetermined threshold or a difference between the pressure value and a desired pressure value does meets or exceed the predetermined threshold. In such examples, the notification may be generated when the pressure values are less than the predetermined threshold or the difference meets or exceeds the predetermined threshold. When the pressure value is less than the predetermined threshold or the difference meets or exceeds the predetermined threshold, this may indicate that the surgical tool 126 has, for example, completed a pass through of hard tissue.

It will be appreciated that in some embodiments, the method 400 may not include the step 416.

The method 400 also comprises causing the motor to stop rotation of the surgical tool (step 420). The motor may be prevented from rotating the surgical tool by the controller or a clutch such as the clutch 302. The controller may stop the motor from rotating the surgical tool when the first value or the second value meets or exceeds the predetermined threshold, when the first value or the second value is below the predetermined threshold, or when a difference between the first value and a desired first value or the second value and a desired second value meets or exceeds the predetermined threshold.

The clutch, as previously described, is configured to prevent the motor from rotating the surgical tool when the value of the sensor data meets or exceeds the predetermined threshold. In such embodiments, the sensor data may comprise torque data and when the torque data meets or exceeds a predetermined torque threshold, the clutch may disengage the motor from the surgical tool. Such disengagement may prevent the surgical tool from applying too much torque to the anatomical element (e.g., hard tissue) and thus, may prevent damage to the anatomical element.

It will be appreciated that in some embodiments, the method 400 may not include the step 420.

The method 400 also comprises causing the robot and/or the robotic arm to stop advancement of the surgical tool (step 424). The surgical tool may not be advanced or may be stopped from further advancement when, for example, the first value or the second value meets or exceeds the predetermined threshold, when the first value or the second value is below the predetermined threshold, or when a difference between the first value and a desired first value or the second value and a desired second value meets or exceeds the predetermined threshold. The surgical tool may be stopped by, for example, the robotic arm and/or the robot stopping advancement of the surgical tool, a user such as a surgeon or other medical provider stopping advancement of the surgical tool, and/or the user providing input to the robot and/or the robotic arm to stop advancement of the surgical tool.

In some embodiments, the first value may be pressure data that can be used as feedback to, for example, the controller to determine when to advance the surgical tool and/or when to stop the surgical tool. For example, the surgical tool may be advanced through hard tissue when the pressure data is consistent with a desired pressure and may be stopped when the pressure data decreases and indicates that the surgical tool has passed through the hard tissue.

It will be appreciated that in some embodiments, the method 400 may not include the step 424.

The present disclosure encompasses embodiments of the method 400 that comprise more or fewer steps than those described above, and/or one or more steps that are different than the steps described above.

As noted above, the present disclosure encompasses methods with fewer than all of the steps identified in FIG. 4 (and the corresponding description of the method 400), as well as methods that include additional steps beyond those identified in FIG. 4 (and the corresponding description of the method 400). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

The following statements provide non-limiting examples of systems and methods for setting and fixing one or more anatomical elements of the present disclosure:

Statement 1. A system for monitoring a surgical tool comprising: a surgical tool configured to perform a task on an anatomical element; a motor configured to rotate the surgical tool; at least one sensor configured to sense at least one value of the surgical tool and yield sensor data; and a controller having a processor and a memory storing data for processing by the processor, the data, when processed, causes the processor to: advance and rotate the surgical tool, receive the sensor data, the sensor data having a first value of the at least one value, convert the sensor data from the first value to a second value, and generate a notification when the second value meets or exceeds a predetermined threshold.

Statement 2. The system of Statement 1, wherein the surgical tool comprises a drilling tool and the task comprises drilling the anatomical element.

Statement 3. The system of Statements 1 or 2, further comprising a printed circuit board (PCB) configured to connect the at least one sensor and the controller.

Statement 4. The system of any preceding Statement, wherein the at least one sensor comprises an accelerometer, the sensor data comprises accelerometer data, the first value comprises acceleration values, and the second value comprises vibration values.

Statement 5. The system of Statement 4, wherein the sensor data is converted using a power spectral density conversion.

Statement 6. The system of any preceding Statement, further comprising a robotic arm configured to orient the surgical tool and advance the surgical tool.

Statement 7. The system of any preceding Statement, wherein the at least one sensor comprises a pressure sensor and the memory stores further data for processing by the processor that, when processed, causes the processor to: cause the motor to stop rotation of the surgical tool when the first value meets or exceeds a predetermined threshold.

Statement 8. The system of any preceding Statement, further comprising a housing configured to house the surgical tool.

Statement 9. The system of Statement 8, wherein the housing forms a tube having an opening through which the surgical tool extends from, wherein debris is suctioned from the opening to a discharge tube.

Statement 10. The system of any preceding Statement, wherein the at least one sensor comprises a pressure sensor and the sensor data comprises pressure data, and wherein the surgical tool is advanced when the pressure data is below the predetermined threshold.

Statement 11. A system for monitoring a surgical tool comprising: a surgical tool configured to drill an anatomical element; a motor configured to rotate the surgical tool; at least one accelerometer configured to sense accelerometer data and yield acceleration sensor data; and a controller having a processor and a memory storing data for processing by the processor, the data, when processed, causes the processor to: cause the motor to rotate and advance the surgical tool, receive acceleration sensor data from the at least one accelerometer, the acceleration sensor data having acceleration values, convert the acceleration values to vibration values, and generate a notification when the vibration values meets or exceeds a predetermined threshold.

Statement 12. The system of Statement 11, wherein the acceleration values are converted using a power spectral density conversion.

Statement 13. The system of Statements 11 or 12, further comprising a robotic arm configured to autonomously operate and orient the surgical tool.

Statement 14. A system for monitoring a surgical tool comprising: a surgical tool configured to drill an anatomical element; a motor configured to rotate the surgical tool; at least one sensor configured to sense at least one value of the surgical tool and yield sensor data; and a controller having a processor and a memory storing data for processing by the processor, the data, when processed, causes the processor to: cause the motor to rotate and advance the surgical tool, receive the sensor data, the sensor data having the at least one value, and generate a notification when the at least one value meets or exceeds a predetermined threshold.

Statement 15. The system of Statement 14, further comprising a clutch configured to prevent the motor from rotating the surgical tool when the at least one value meets or exceeds the predetermined threshold.

Statement 16. The system of Statements 14 or 15, wherein the at least one sensor comprises a pressure sensor and the memory stores further data for processing by the processor that, when processed, causes the processor to: cause the motor to stop rotation of the surgical tool when the at least one value meets or exceeds a predetermined threshold.

Statement 17. The system of any preceding Statement, further comprising a housing configured to house the surgical tool.

Statement 18. The system of Statement 17, further comprising a camera positioned on the housing.

Statement 19. The system of Statement 17, wherein the housing forms a tube having an opening through which the surgical tool extends from, wherein debris is suctioned from the opening to a discharge tube.

Statement 20. The system of any preceding Statement, wherein the at least one sensor comprises a pressure sensor and the sensor data comprises pressure data, and wherein the surgical tool is advanced when the pressure data is below the predetermined threshold.

What is claimed is:

1. A system for monitoring a drill, the system comprising:
   the drill configured to perform a task on an anatomical element;
   a motor configured to rotate a drill bit;
   one or more bearings;
   at least one sensor configured to sense at least one value associated with the one or more bearings and yield sensor data; and
   a controller having a processor and a memory storing data for processing by the processor, wherein the data, when processed, causes the processor to:
   advance the drill towards the anatomical element and rotate the drill bit using the motor,
   receive the sensor data, the sensor data having a first value of the at least one value,
   convert the sensor data from the first value to a second value,
   compare the second value to a nominal value, and
   generate a notification associated with the one or more bearings when the second value exceeds the nominal value.

2. The system of claim 1, further comprising a printed circuit board (PCB) configured to connect the at least one sensor and the controller.

3. The system of claim 1, wherein the at least one sensor comprises an accelerometer, the sensor data comprises accelerometer data, the first value comprises acceleration values, and the second value comprises vibration values.

4. The system of claim 3, wherein the sensor data is converted using a power spectral density conversion.

5. The system of claim 1, further comprising a robotic arm configured to orient the drill and advance the drill.

6. The system of claim 1, wherein the drill further comprises a pressure sensor and the memory stores further data for processing by the processor that, when processed, causes the processor to:
   compare a first pressure value to an expected pressure value; and
   cause the motor to stop rotation of the drill when the first pressure value decreases from the expected pressure value.

7. The system of claim 6, wherein the drill is advanced when the first pressure value is consistent with the expected pressure value.

8. The system of claim 1, further comprising a housing configured to house the drill bit.

9. The system of claim 8, wherein the housing forms a tube having an opening through which the drill bit extends from, wherein debris is suctioned from the opening to a discharge tube.

10. The system of claim 1, wherein comparing the second value to the nominal value yields a difference between the second value and the nominal value and the data further causes the processor to compare the difference to a predetermined threshold and generate the notification to indicate a failure of the one or more bearings when the difference meets or exceeds the predetermined threshold.

11. A system for monitoring a surgical tool comprising:
   a surgical tool configured to drill an anatomical element, wherein the surgical tool comprises one or more bearings;
   a motor configured to rotate a drill bit of the surgical tool;
   at least one accelerometer configured to sense accelerometer data and yield acceleration sensor data associated with the one or more bearings; and
   a controller having a processor and a memory storing data for processing by the processor, the data, when processed, causes the processor to:
   cause the motor to rotate and advance the surgical tool,
   receive acceleration sensor data from the at least one accelerometer, the acceleration sensor data having acceleration values,
   convert the acceleration values to vibration values, and
   generate a notification when the vibration values exceeds a nominal value.

12. The system of claim 11, wherein the acceleration values are converted using a power spectral density conversion.

13. The system of claim 11, further comprising a robotic arm configured to autonomously operate and orient the surgical tool.

14. A system for monitoring a surgical tool comprising:
   a surgical tool configured to drill an anatomical element, wherein the surgical tool includes one or more bearings;
   a motor configured to rotate a drill bit of the surgical tool;
   at least one sensor configured to sense at least one value associated with the one or more bearings and yield sensor data; and
   a controller having a processor and a memory storing data for processing by the processor, the data, when processed, causes the processor to:
   cause the motor to rotate and advance the surgical tool,
   receive the sensor data, the sensor data having the at least one value, and generate a notification when the at least one value associated with the one or more bearings exceeds a nominal value.

15. The system of claim 14, further comprising a clutch configured to prevent the motor from rotating the surgical tool when the at least one value associated with the one or more bearings exceeds the nominal value.

16. The system of claim 14, wherein the surgical tool further comprises a pressure sensor to sense and yield pressure data and the memory stores further data for processing by the processor that, when processed, causes the processor to:

cause the motor to stop rotation of the surgical tool when a first pressure value decreases from a predetermined pressure threshold.

17. The system of claim 16, wherein the surgical tool is advanced when the pressure data is consistent with the predetermined pressure threshold.

18. The system of claim 14, further comprising a housing configured to house the drill bit.

19. The system of claim 18, further comprising a camera positioned on the housing.

20. The system of claim 18, wherein the housing forms a tube having an opening through which the drill bit extends from, wherein debris is suctioned from the opening to a discharge tube.

\* \* \* \* \*